United States Patent [19]

Nishiura et al.

[11] Patent Number: 5,698,590
[45] Date of Patent: Dec. 16, 1997

[54] PROSTAGLANDIN DERIVATIVES

[75] Inventors: Akio Nishiura; Takuya Seko; Ryoji Matsumoto; Shin-ichi Hamano, all of Osaka, Japan

[73] Assignee: Ono Pharmaceutical Co., Ltd., Osaka, Japan

[21] Appl. No.: 701,486

[22] Filed: Aug. 22, 1996

[30] Foreign Application Priority Data

Aug. 25, 1995 [JP] Japan ................................ 7-238984

[51] Int. Cl.$^6$ .................. C07C 405/00; H01K 31/557
[52] U.S. Cl. ............. 514/530; 424/450; 554/228; 560/121
[58] Field of Search ............. 560/121; 554/228; 514/530; 424/450

[56] References Cited

FOREIGN PATENT DOCUMENTS 1322637  7/1973  United Kingdom .

Primary Examiner—Robert Gerstl
Attorney, Agent, or Firm—Watson Cole Stevens Davis, PLLC

[57] ABSTRACT

Prostaglandin $E_1$ ester derivatives of the formula (I):

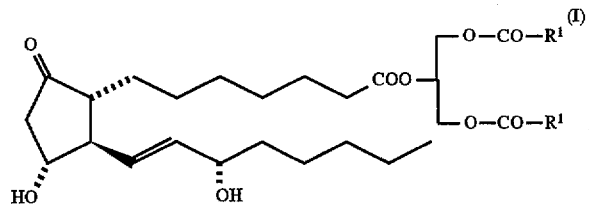

wherein the R' groups are the same as each other and are C4–12 alkyl; or cyclodextrin clathrates thereof, liposome formulations containing them, and pharmaceutical compositions containing them, as active ingredient.

The compounds of formula (I) have the effect of increasing blood flow and are useful for the prevention and/or treatment of peripheral circulatory disorder, decubitus, or skin ulcers, or for the maintenance of blood flow.

8 Claims, No Drawings

PROSTAGLANDIN DERIVATIVES

BACKGROUND OF THE INVENTION

The present invention relates to prostaglandin $E_1$ (hereinafter abbreviated as $PGE_1$) ester derivatives or cyclodextrin clathrates thereof, liposome formulations containing them, and pharmaceutical compositions containing them as active ingredient.

$PGE_1$ is represented by the following structural formula:

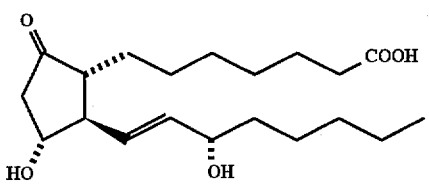

and has various physiological properties. In particular, $PGE_1$ has a hypotensive, vasodilatory, blood flow increasing and anti-platelet effect on blood vessels.

Because of its various physiological properties, $PGE_1$ has been applied in medicine. Already, $PGE_1$ has been used for treatment of peripheral arterial occlusive disease, thrombotic anginetic obliterence, etc., and for maintenance of blood flow after reconstructive vascular surgery, maintenance of low blood pressure levels during a surgical operation, as an anesthetic, etc.

Peripheral circulatory disorder is a disease accompanied by various ischemic symptoms such as pain, psychoresthesia, etc., in which obstructions are induced by thrombus formation in peripheral blood vessels, and following ulcer formation. In order to treat this disorder, it is necessary to improve the blood circulation by increasing blood flow in the peripheral circulation.

Because $PGE_1$ increases blood flow, it could be useful for treating peripheral circulatory disorder. However, the usefulness of $PGE_1$ in this regard is limited by the following phenomena:

(1) $PGE_1$ has many physiological properties. Therefore, if one physiological action of $PGE_1$ is applied to the therapy, other physiological properties of $PGE_1$ become side effects.

(2) $PGE_1$ is rapidly inactivated by its metabolizing enzyme in vivo.

Thus, if a large amount of $PGE_1$ is injected into the blood vessel at once, it acts not only on the peripheral circulation but also on the aortic series; therefore, there is a fear of causing serious hypotension. In order to prevent this problem, $PGE_1$ should be injected in controlled doses so that it acts on the peripheral circulation, but acts to a lesser degree on the aortic series.

On the other hand, it is known that $PGE_1$ is very rapidly metabolized. Accordingly, in order to maintain its blood flow increasing effect, it is required that $PGE_1$ be sequentially administered in vivo.

As a result of considering these phenomena in combination, it is desired to prepare a compound that is converted into $PGE_1$ in vivo after its administration. Furthermore, the rate of conversion should be moderately slow, so that the blood flow increasing effect can be maintained.

Compounds which display physiological effects for a prolonged period compared to that provided by $PGE_1$ are described in the specification of Great Britain Patent No. 1322637, herein incorporated by reference. These compounds have the formula (B):

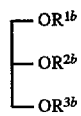

in which $R^{1b}$, $R^{2b}$ and $R^{3b}$ represent, inter alia, hydrogen, stearoyl ($-CO(CH_2)_{16}CH_3$) or palmitoyl ($-CO(CH_2)_{14}CH_3$), or the formula ($B_1$):

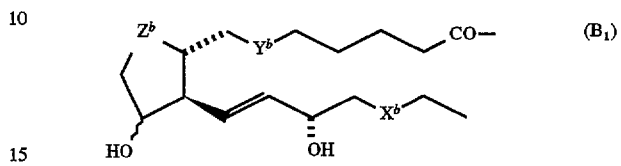

in which $X^b$ represents, inter alia, $-CH_2CH_2-$, $Y^b$ represents, inter alia, $-CH_2CH_2-$, $Z^b$ represents, inter alia, $-CO-$, and at least one of $R^{1b}$, $R^{2b}$, and $R^{3b}$ represents the group shown by the formula ($B_1$).

The present inventors have searched for a compound that is gradually converted into $PGE_1$ in vivo after administering. As a result, the present inventors have found that this result may be achieved with the compounds in which the carboxylic acid group at the 1-position of $PGE_1$ is esterified by a specific alcohol.

Further, the present inventors have also found that the effect may be improved by enclosing the compounds of the present invention in a closed vesicle comprising a phospholipid bilayer called a liposome.

SUMMARY OF THE INVENTION

The present invention accordingly provides prostaglandin $E_1$ ester derivatives of formula (I):

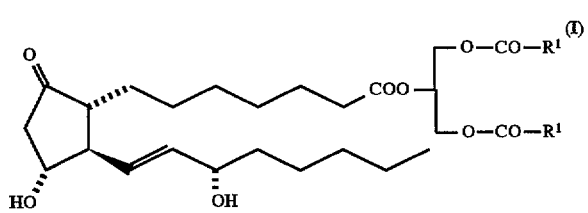

wherein the groups $R_1$ are the same as each other and are C4–C12 alkyl; or cyclodextrin clathrates thereof.

The compounds of formula (I) have excellent selectivity and maintenance of action.

The present invention also provides liposome formulations comprising a compound of formula (I) or a cyclodextrin clathrate thereof as an active ingredient. Such lipsome formulations display excellent maintenance of activity and release of the active ingredient.

The invention also includes pharmaceutical compositions comprising a compound of formula (I) or a cyclodextrin clathrate thereof as an active ingredient.

$PGE_1$ derivatives of formula (I) are different from those of formula (B). In the compounds of formula (B), the only acyl groups represented by $R^{1b}$, $R^{2b}$ and $R^{3b}$ are stearoyl and palmitoyl, while the corresponding part of the compounds of the present invention of formula (I) is a C5–13 acyl group.

DETAILED DESCRIPTION OF THE INVENTION

Throughout the specification, it will be understood by those skilled in the art that all isomers are included in the present invention. For example, the term "alkyl group" includes straight-chain groups and branched-chain groups.

In the formula (I), a C4–12 alkyl group represented by $R^1$ is butyl, pentyl, hexyl, heptyl, octyl, nonyl, decyl, undecyl, dodecyl or an isomer thereof.

Preferably, $R^1$ is C4–6 alkyl, C10–12 alkyl, or an isomer thereof. More preferably, $R^1$ is pentyl or undecyl.

Cyclodextrin clathrates of the $PGE_1$ derivatives of the formula (I) may be prepared by the method described in the specification of U.S. Pat. No. 3,816,393 or 4,054,736, both of which are herein incorporated by reference, using α-, β- or γ- cyclodextrins or a mixture thereof.

Converting $PGE_1$ derivatives of the formula (I) into their cyclodextrin clathrates serves to increase their stability and solubility in water, and is therefore beneficial because it facilitates administration of the invention compounds as pharmaceuticals.

Compounds of formula (I) may be prepared by the elimination of the $R^2$ group of a compound of formula (II):

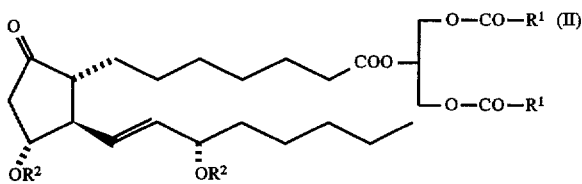

in which $R^1$ is as defined for formula (I), and $R^2$ is a hydroxyl-protecting group which may be eliminated under acidic conditions, for example, with tetrahydropyran-2-yl, methoxymethyl or 2-ethoxyethyl. The elimination reaction of the $R^2$ group may be carried out in an aqueous solution of organic acid (e.g., acetic acid or p-toluenesulfonic acid) or inorganic acid (e.g., hydrochloric acid or sulfuric acid), in the presence of a water-miscible organic solvent (e.g., a lower alkanol such as methanol or ethanol) or an ether (e.g., dioxane or tetrahydrofuran) at a temperature between room temperature and 75° C. The above-mentioned reaction is preferably carried out in a mixed solvent comprising acetic acid, water and tetrahydrofuran at a temperature of 40° C. to 50° C.

The compounds of formula (II) may be prepared by reacting a compound of formula (III):

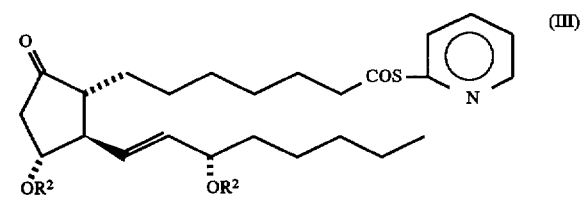

in which $R^2$ is as hereinbefore defined, with a compound of formula (IV):

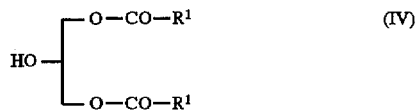

in which $R^1$ is as hereinbefore defined, without a solvent at a temperature of 50° C. to 100 C.

The compounds of formula (III) may be prepared by reacting a free carboxylic acid corresponding to a compound of formula (II) with 2,2-dipyridyl disulfide in organic solvent (e.g., acetonitrile) in the presence of triphenylphosphine at a temperature between 50° C. and the reflux temperature of the solvent.

The compounds of the formula (II) may be also prepared by reacting a free carboxylic acid corresponding to a compound of formula (II) with a compound of formula (IV) in an organic solvent (e.g., tetrahydrofuran) in the presence of a tertiary amine (e.g., triethylamine) using a condensing agent (e.g., 1-(3-dimethylaminopropyl)-3-ethylcarbodiimide (EDC) or 4-dimethylaminopyridine (DMAP)) at a temperature of 0° C. to 40° C.

One of the free carboxylic acids used to prepare compounds of formula (II) is (13E)-(11α, 15S)-9-oxo-11, 15-bis (tetrahydropyran-2-yloxy) prost-13-enoic acid, which is a known compound described in J. Am. Chem. Soc., 92,2586 (1970), herein incorporated by reference.

The other free carboxylic acids corresponding to the compounds of formula ((II), and the compounds of formula (IV), are known per se or may be easily prepared from known compounds by methods known per se, e.g., the method described in J. Org. Chem. 35,2082 (1970), herein incorporated by reference.

Concretely, for example, compounds of formula (IV) may be prepared by the method described in the following Scheme.

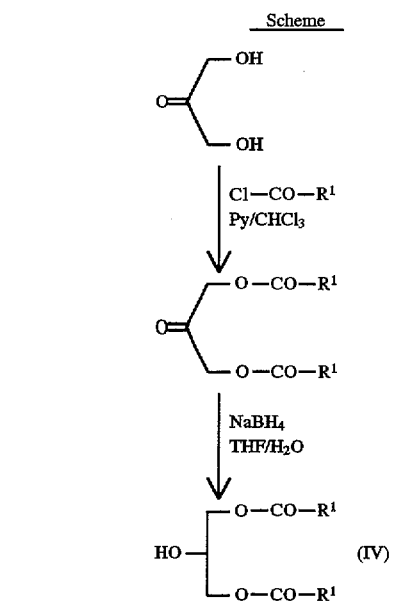

In the above Scheme, Py is pyridine, THF is tetrahydrofuran, and R' is as hereinbefore defined.

In spite of having a potent and maintainable blood flow increasing effect, $PGE_1$ ester derivatives of the formula (I), and cyclodextrin clathrates thereof, have only a weak hypotensive effect, and therefore, may be used as agents for the prevention and/or treatment of peripheral circulatory disorder (e.g., peripheral arterial occlusive disease or thrombotic anginetic obliterence), decubitus, skin ulcers (e.g., ulcers resulting from burns, diabetic ulcers, stenosis of femoral artery and operation stress), and for the maintenance of blood flow after reconstructive vascular surgery.

The blood flow increasing effect and hypotensive effect of the compounds of the present invention were determined by the following experiments.

EXAMPLE

Male rats weighing 200–350 g were anesthetized with urethane (25% urethane, 6 ml/kg, s.c.). The carotid artery and jugular vein were cannulated with polyethylene tubes for measurement of blood pressure and for drug injection, respectively. Blood pressure was obtained with a disposable pressure transducer kit (Spectramed, Ltd) and recorded with a recticoder (model RJG-4128, Nihon kohden, Ltd). Also, blood flow was monitored as cutaneous blood flow of the dorsum pedis using an attachment-type laser-Doppler flowmeter (model ALF21, Advance, Ltd). Measurements were taken until the values recovered to the level observed before injection of drugs. Injection time was about 10 seconds. The hypotensive effect and blood flow increasing effect were calculated as the maximum hypotensive activity (mmHg) and the area under the curve (AUC) after injection of drugs, respectively.

The results were represented by the dose required to obtain an effective increase in blood flow (main effect), and by the hypotensive effect (side effect) at the same dose.

The compounds of the present invention were administered in the form of liposome formulations (as prepared in Example 3 below). As a comparative compound, $PGE_1$ 1,3-bis(palmitoyloxy)-2-propyl ester (described in Example 1 of the specification of Great Britain Patent No. 1322637) was dissolved with β-cyclodextrin as solubilizer, and was administered. The solubility of this comparative compound was very low; thus, administration without solubilizer was impossible.

The effectiveness of increasing blood flow was determined by the following method. It is known that a commercially available $PGE_1$ lipid emulsion shows efficacy at 5 μg/kg i.v. injection in the rat disease model [described in Drug Exp. Clin. Res., 12, 917 (1986), herein incorporated by reference]. In the above described experimental assessment system for the compounds of the present invention, the AUC for this $PGE_1$ lipid emulsion (5 μg/kg, i.v.) was 771 on the blood flow increasing effect; thus, this value was chosen as an effective value for the increase in blood flow.

The results of this experiment are shown in Table I, below.

For the above described purposes, compounds of the formula (I), and cyclodextrin clathrates of them, may be normally administered systemically or partially, usually by parenteral administration.

The doses to be administered are determined depending upon, for example, age, body weight, symptom, the desired therapeutic effect, the route of administration, and the duration of the treatment. In the human adult, the doses per person are generally from 0.1 μg to 500 μg, by parenteral administration (preferably intravenous administration), up to several times per day, or continuous administration for from 1 to 24 hrs. per day intravenously.

As mentioned above, the doses to be used depend upon various conditions. Therefore, there are cases in which doses lower than or greater than the ranges specified above may be used.

The compounds of the present invention may be administered in the form of, for example, injections, liniments or suppositories for parenteral administration.

Injection formulations for parenteral administration include sterile aqueous or nonaqueous solutions, suspensions and emulsions. Aqueous solutions and suspensions may include distilled water for injection or physiological salt solution. Non-aqueous solutions and suspensions may, for example, include propylene glycol, polyethylene glycol, vegetable oil such as olive oil, alcohol such as ethanol or POLYSORBATE80.®

These injection formulations may comprise additional ingredients other than inert diluents; e.g., preserving agents, wetting agents, emulsifying agents, dispersing agents, stabilizing agents, and assisting agents, e.g., agents to assist dissolution (e.g., glutamic acid or aspartic acid).

These formulations may be sterilized, for example, by filtration through a bacteria-retaining filter, by incorporation of sterilizing agents in the compositions, or by irradiation.

TABLE 1

| | | Blood flow increasing effect | | | Hypotensive effect | | |
|---|---|---|---|---|---|---|---|
| Example | Dose (μg/kg) | Total AUC | Dose (A) required to obtain AUC = 771 (μg/kg) | Relative activity (X) | Maximum hypotension (mmHg) | Maximum hypotension on dose (A) (mmHg) | Relative activity (X) |
| 1 | 1 | 116 | 3.6 | 6.6 | 0 | 2.2 | 0.31 |
|  | 3 | 483 |  |  | 1 |  |  |
|  | 10 | 2566 |  |  | 9 |  |  |
| 2 | 1 | 185 | 2.2 | 10.7 | 4 | 6.7 | 0.94 |
|  | 3 | 1206 |  |  | 9 |  |  |
|  | 10 | 3919 |  |  | 19 |  |  |
| Comparative compound | 3 | 350 | 23.6 | 1 | 1 | 7.1 | 1 |
|  | 10 | 710 |  |  | 6 |  |  |
|  | 30 | 830 |  |  | 8 |  |  |

Table 1 shows the following facts:

(1) Blood flow increasing effect (main effect) of the compounds of the present invention is about 7 to 11 times better than that of the comparative compound.

(2) On the other hand, hypotensive effect (side effect) of the compounds of the present invention at the effective dose is 0.94 to 0.31 times that of the comparative compound.

Therefore, the compounds of the present invention are significantly better than the comparative compound for the prevention and/or treatment of peripheral circulatory disorder, decubitus, skin ulcers, or for blood flow maintenance after reconstructive vascular surgery.

The toxicity of the compounds of the present invention is very low and therefore the compounds of the present invention may be suitable for pharmaceutical use.

They may also be manufactured in the form of sterile solid compositions which may be dissolved in sterile water or some other sterile diluent(s) for injection immediately before use.

Other compositions for parenteral administration include liquids for external use, and endermic liniments, ointment, suppositories for rectal administration and pessaries for vaginal administration which comprise one or more of the active compound(s) and may be prepared by methods known per se.

Furthermore, the present invention includes liposome formulations containing $PGE_1$ ester derivatives of the formula (I) or cyclodextrin clathrates thereof, as active ingredient.

The liposomes used in these formulations are uni or multilamellar fine spherical vesicles comprising phosphatidylcholine (e.g., natural phospholipids derived from egg yolk or soya bean, and synthetic phospholipids such as dimyristoylphosphatidylcholine, distearoylphosphatidylcholine and dipalmitoylphosphatidylcholine) as the liposome membrane material. The encapsulation of the drugs into the liposomes enables delivery of the drugs to the targeted organ, and prolonged release of the drugs.

Additives other than the active ingredient, which are, for example, sugars (e.g., lactose or mannitol), neutral phospholipids (e.g., cholesterol or triglyceride) or charged lipids (e.g., phosphatidic acid or stearylamine) can be mixed into the liposome formulations.

The liposome formulations may be prepared by methods known per se. For example, suitable methods are described in detail in LIposome Technology, Vol. 1, 2 and 3, edited by Gregoriadis., G (published in 1993), herein incorporated by reference.

The following Reference Examples and Examples illustrate, but do not limit, the present invention.

The solvents in the parentheses show the developing or eluting solvents and the ratios of the solvents used are by volume in chromatographic separations.

The solvents in the parentheses in NMR show the solvents used for measurement.

REFERENCE EXAMPLE 1

1,3-bis(dodecanoyloxy)-propan-2-one

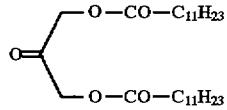

To a suspension of 1,3-propanediol-2-one (2.31 g) in chloroform (100 ml) was added dodecanoyl chloride (16.5 g), and then pyridine (8.5 ml) was added dropwise thereto slowly. After stirring for 12 hours at room temperature, a yellowish milky mixture was obtained. This mixture was added to ice water and the solution was extracted with dichloromethane (twice). The organic layer was washed with a saturated aqueous solution of sodium bicarbonate and a saturated aqueous solution of sodium chloride, successively, dried over magnesium sulfate and evaporated. The yellow solid was dissolved into methanol, the impurities removed by filtration, and then the filtrate was crystallized to give the title compound (7.3 g) as a white crystal having the following physical data.

TLC:Rf 0.55 (n-hexane:ethyl acetate=4:1),

NMR (CDCl$_3$) :δ4.75 (4H, s), 2.42 (4H,t, J=7.2 Hz), 1.66 (4H, m), 1.27 (32H, m), 0.88 (9H, t, J=7.2 Hz).

REFERENCE EXAMPLE 2

1,3-bis (dodecanoyloxy)-2-propanol

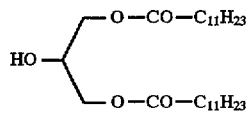

To a solution of the 2-oxo derivative prepared in Reference Example 1 (3.8 g) in tetrahydrofuran (THF) (100 ml) was added water (7 ml). Sodium borohydride (477 mg) was added to the reaction solution at room temperature and the solution was stirred for 30 min. Ice water was added to the reaction mixture and the diluted reaction mixture was extracted with a solvent mixture of ethyl acetate and n-hexane (1:1). The organic layer was washed with a saturated aqueous solution of sodium chloride, dried over magnesium sulfate and evaporated. The residue was purified by silica gel column chromatography (ethyl acetate:n-hexane= 5:1) to give the title compound (2.78 g) having the following physical data.

TLC:Rf 0.45 (n-hexane:ethyl acetate;=4:1).

NMR (CDCl$_3$) :δ4.28–4.02 (5H, m), 2.36 (4H, t, J=7.0 Hz), 1.62 (4H, m), 1.26 (32H, m), 0.88 (9H, t, J=7.2 Hz).

REFERENCE EXAMPLE 3

(13E)-(11α, 15S)-9-oxo-11, 15-bis(tetrahydropyran-2-yloxy)prost-13-enoic acid pyridin-2-ylthio ester

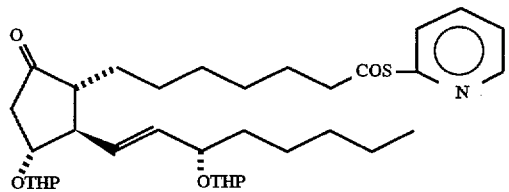

To a solution of (13E)-(11α, 15S)-9-oxo-11, 15-bis (tetrahydropyran-2yloxy)prost-13-enoic acid (808 mg) in acetonitrile (15 ml) was added triphenylphosphine (532 mg) and 2,2'-dipyridyl disulfide (448 mg), successively, and the solution was refluxed for 1 hour. The solvent was distilled off and the residue was purified by silica gel column chromatography (n-hexane:ethyl acetate=2:1) to give the title compound (743 mg) having the following physical data.

TLC:Rf 0.28 (n-hexane:acetic acid=1:1).

EXAMPLE 1

PGE$_1$ 1,3-bis (dodecanoyloxy)-2-propyl ester

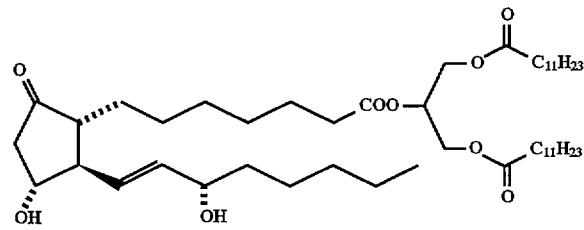

A mixture of the thio ester derivative prepared in Reference Example 3 (743 mg) and the alcohol derivative prepared in Reference Example 2 (703 mg) was heated at 70°–80° C. for 18 hours without a solvent. After the temperature of the mixture was cooled to room temperature, the mixture was purified by silica gel chromatography (n-hexane:ethyl acetate=2:1) to give PGE$_1$ 1,3-bis (dodecanoyloxy)-2-propyl ester 11, 15-bis(tetrahydropyran-2-yl)ether and the starting material (alcohol derivative).

The above mixture was dissolved into THF (0.5 ml), 87.5% acetic acid (3 ml) was added to the resulting solution, and the solution was stirred for 2 hours at 80° C. After the temperature of the mixture was cooled to room temperature, water was added thereto, and it was extracted with ethyl acetate. The extract was washed with water, a saturated aqueous solution of sodium bicarbonate, and a saturated aqueous solution of sodium chloride, successively, dried over magnesium sulfate and evaporated. The residue was purified by silica gel chromatography (n-hexane:ethyl acetate=1:1–1:3) to give the title compound (2.78 g) having the following physical data. TLC:Rf 0.68 (n-hexane:ethyl acetate=1:3), NMR (CDCl$_3$) :δ5.78–5.48 (2H, m), 5.30–5.18 (1H, m), 4.32 (2H, dd, J=12,6.0 Hz), 4.24–4.00 (4H, m), 3.20–2.80 (1H, bs), 2.72 (1H, dd, J=12, 7.5 Hz), 2.42–2.15 (9H, m), 2.15–1.90 (2H, m), 1.90–1.48 (10H, m), 1.48–1.18 (42H, m), 1.00–0.90 (9H, m).

EXAMPLE 2

PGE$_1$ 1,3-bis (hexanoyloxy)-2-propyl ester

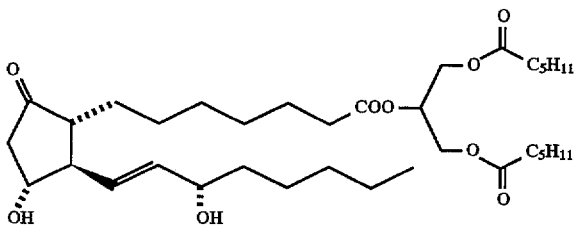

By the same procedures as in Reference Example 1, Reference Example 2, and Example 1, starting from caproyl chloride instead of dodecanoyl chloride, the title compound having the following physical data was obtained.

NMR (CDCl$_3$) :δ5.78–5.50 (2H, m), 5.38–5.20 (1H, m), 4.32 (2H, dd, J=12,4.0 Hz), 4.24–4.00 (4H, m), 3.30–2.80 (1H, bs), 2.72 (1H, dd, J=12, 7.5 Hz), 2.42–2.15 (7H, m), 2.15–1.90 (2H, m), 1.90–1.48 (8H, m), 1.48–1.18 (22H, m), 1.00–0.90 (9H, m).

EXAMPLE 3

Further method of synthesis of PGE$_1$ 1,3-bis (hexanoyloxy)-2-propyl ester

To a solution of (13E)-(11α, 15S)-9-oxo-11, 15-bis (tetrahydropyran-2-yloxy)prost-13-enoic acid (2.54 g) in THF (5 ml) were added 1,3-bis (hexanoyloxy)-2-propanol (2.01 g) and EDC (1.43 g), successively. Under cooling with ice, to the mixture was added triethylamine (1.6 ml) slowly, and then added DMAP (15 mg). After the mixture was stirred for 3.5 hours at room temperature, water was added to the mixture to stop the reaction. The reaction mixture was extracted with ethyl acetate. The organic layer was dried over a saturated aqueous solution of sodium chloride, and then dried over magnesium sulfate and evaporated. The residue was purified by silica gel chromatography (n-hexane:ethyl acetate=5:1) to give the mixture of PGE$_1$ 1,3-bis (hexanoyloxy)-2-propyl ester 11, 15-bis (tetrahydropyran-2-yloxy) ether and the starting material (alcohol derivative). This mixture was dissolved into THF (3 ml), and 87.5% acetic acid (12 ml) was added thereto and it was stirred for 2 hours at 80° C. After the temperature of the mixture was cooled to room temperature, water was added thereto, and it was extracted with ethyl acetate. The extract was washed with water, a cooled saturated aqueous solution of sodium bicarbonate, and a saturated aqueous solution of sodium chloride, successively, dried over magnesium sulfate and evaporated. The residue was purified by silica gel chromatography (n-hexane:ethyl acetate=1:1–1:4) to give the title compound (1.62 g) having the physical data as described in Example 2.

EXAMPLE 4

Preparation of the Liposome Formulations

Dimyristoylphosphatidylcholine (DMPC) (6 mg) and various PGE$_1$ ester derivatives of the present invention (3–90 µg) were dissolved in chloroform and a dry lipid film of the mixture was produced by freeze-drying, i.e., removing the chloroform and standing the mixture under reduced pressure for one hour.

The dry lipid film was dispersed into a 10% maltose solution (3 ml) by using a vortex mixer (type S-100, Taiyokagaku Inc.) and an aqueous suspension with a drug concentration of 1, 3, 10, or 30 µg/ml was obtained. The obtained multilamellar liposome solutions (3 ml) were transferred into plastic tubes and then sonicated with a probe sonicator (type: SONIFIER cell disruptor 200, Branson) at the condition of 50% pulsed operation for 15 minutes. The sonicated solutions were passed through a membrane filter with a pore diameter of 0.2 µm to remove titanium particles and liposome formulations with a mean diameter of 40–70 nm were formed.

FORMULATION EXAMPLE 1

The liposome formulations of PGE$_1$ 1,3-bis (dodecanoyloxy)-2-propyl ester (prepared in Example 3) were divided into 1 ml vials and lyophilized to generate injection products.

We claim:

1. A prostaglandin E$_1$ ester derivative of formula (I):

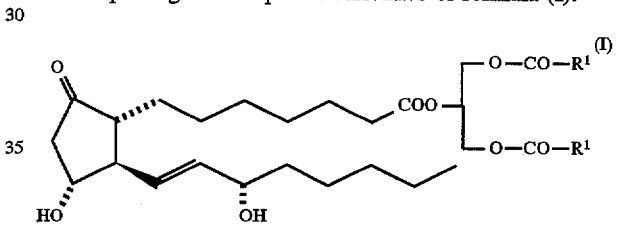

wherein the R$^1$ groups are the same as each other and are C4–12 alkyl; or a cyclodextrin clathrate thereof.

2. A compound according to claim 1 which is PGE$_1$ 1,3-bis (hexanoyloxy)-2-propyl ester or PGE$_1$ 1,3-bis (dodecanoyloxy)-2-propyl ester.

3. A liposome formulation comprising: a PGE$_1$ ester derivative of formula (I) as defined in claim 1, or a cyclodextrin clathrate thereof, as active ingredient; and a liposome membrane material.

4. A liposome formulation according to claim 3, wherein the liposome membrane material comprises dimyristoylphosphatidylcholine.

5. A liposome formulation according to claim 3, wherein the liposome membrane material comprises egg lecithin.

6. A liposome formulation according to claim 3, wherein the PGE$_1$ ester derivative is PGE$_1$ 1,3-bis (hexanoyloxy)-2-propyl ester or PGE$_1$ 1,3-bis (dodecanoyloxy)-2-propyl ester.

7. A pharmaceutical composition which comprises, as active ingredient, an effective amount of a prostaglandin E$_1$ derivative of formula (I) as defined in claim 1, or a cyclodextrin clathrate thereof.

8. A method for the prevention and treatment of peripheral circulatory disorder, decubitus, or skin ulcers, or for blood flow maintenance after reconstructive vascular surgery, which comprises administering an effective amount of a prostaglandin E$_1$ derivative of formula (I) as defined in claim 1, or a cyclodextrin clathrate thereof.

* * * * *